Figure 1:
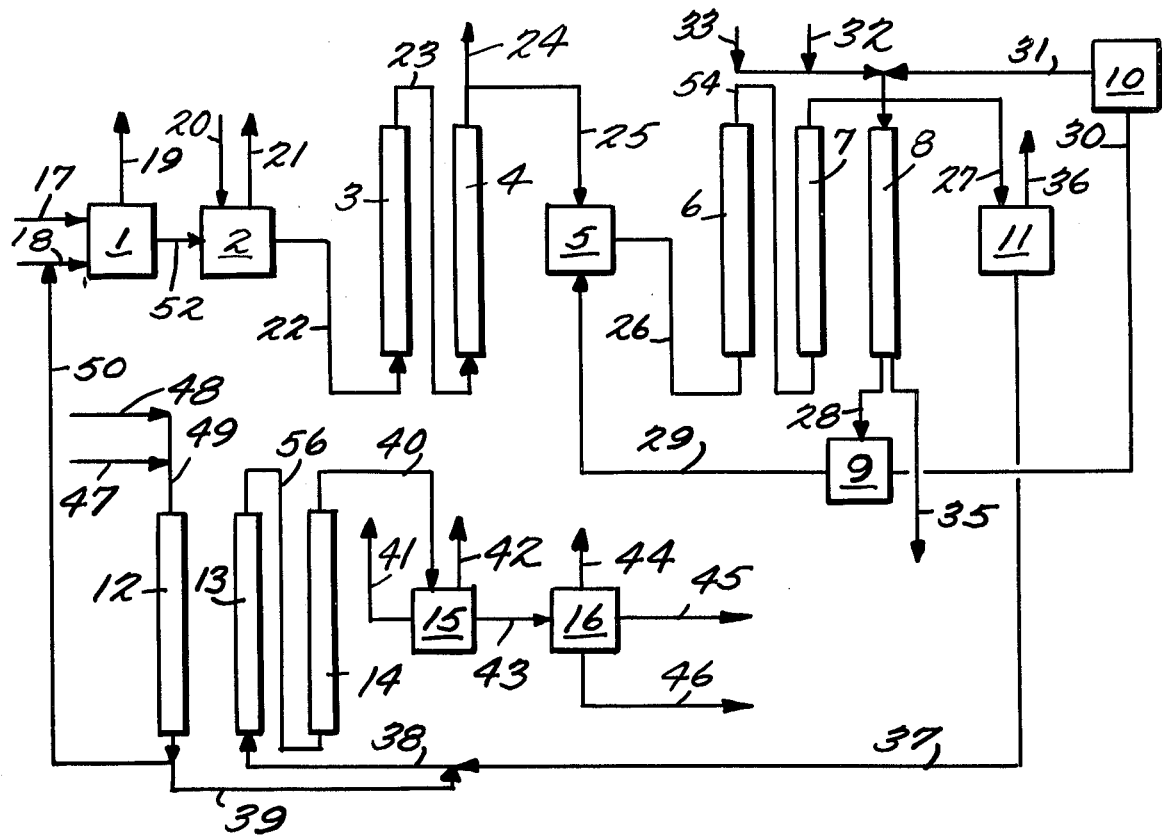

United States Patent [19]

Prescher et al.

[11] 4,150,241

[45] * Apr. 17, 1979

[54] PROCESS FOR THE PRODUCTION OF PURE RACEMIC ACID AND MESOTARTARIC ACID AND SEPARATION OF MALEIC ACID FROM SYNTHETIC TARTARIC ACID

[75] Inventors: Günter Prescher; Gerd Schreyer, both of Hanau, Fed. Rep. of Germany

[73] Assignee: Deutsche Gold- und Silber-Scheideanstalt vormals Roessler, Frankfurt, Fed. Rep. of Germany

[ * ] Notice: The portion of the term of this patent subsequent to Sep. 13, 1994, has been disclaimed.

[21] Appl. No.: 656,591

[22] Filed: Feb. 9, 1976

[30] Foreign Application Priority Data

Feb. 26, 1975 [DE] Fed. Rep. of Germany ....... 2508228
Sep. 29, 1975 [DE] Fed. Rep. of Germany ....... 2543332

[51] Int. Cl.² ............................................. C07C 59/14
[52] U.S. Cl. ..................................... 562/585; 562/595
[58] Field of Search .................. 260/536; 562/585, 595

[56] References Cited

U.S. PATENT DOCUMENTS 2,437,648  3/1948  Milas ..................................... 260/536
3,875,223  4/1975  Yonemitsu et al. ................... 260/536

FOREIGN PATENT DOCUMENTS 214055   2/1973  Fed. Rep. of Germany ........... 260/536
1183449  3/1970  United Kingdom ..................... 260/536

Primary Examiner—Paul J. Killos
Attorney, Agent, or Firm—Cushman, Darby & Cushman

[57] ABSTRACT

Pure racemic acid (dl-tartaric acid) and meso tartaric acid are produced by reaction of an alkali maleate with aqueous hydrogen peroxide in the presence of an alkali tungstate in a process wherein the molar ratio of hydrogen peroxide to maleic acid is greater than 1:1 and the alkali salt of cis-epoxysuccinic acid formed together with the alkali tungstate, in a given case after destroying the excess hydrogen peroxide, are converted to free cis-epoxysuccinic acid and free tungstic acid by leading them over a strongly acidic cation exchanger, whereupon the hydrolysis of the free cis-epoxysuccinic acid to racemic acid and meso-tartaric acid can take place either in the presence of or the absence of the free tungstic acid, whereby the tungstic acid in the case of catalyst free hydrolysis before, and in the case of catalyst containing hydrolysis after this hydrolysis is removed with an anion exchanger and the racemic acid is then in known manner crystallized out of the tungstic acid free hydrolysis mixture by lowering the temperature in a given case with evaporation of water, whereupon the meso-tartaric acid remains in the mother liquor, and there is recovered from the mother liquor either by crystallization or by evaporation to dryness, in a given case in admixture with racemic acid, unreacted cis-epoxysuccinic acid and maleic acid, while the anion exchanger laden with the tungstic acid is regenerated in known manner with dilute aqueous alkali and, in a given case, the resulting solution of alkali tungstate, eventually after treatment with activated carbon is returned directly into the epoxidation step.

There is also disclosed a process for the separation of maleic acid from synthetic tartaric acid containing maleic acid in which an aqueous solution of the crude tartaric acid which can also still contain the catalyst used, is led over a basic anion exchanger which is present in the hydroxyl or tartrate form.

37 Claims, 2 Drawing Figures

PROCESS FOR THE PRODUCTION OF PURE RACEMIC ACID AND MESOTARTARIC ACID AND SEPARATION OF MALEIC ACID FROM SYNTHETIC TARTARIC ACID

In its first aspect the invention is directed to a process for the production of racemic acid (dl-tartaric acid) and meso-tartaric acid by epoxidation of alkali salts of maleic acid with hydrogen peroxide in the presence of an alkali tungstate in an aqueous medium at elevated temperature, conversion to the free acid and subsequent hydrolysis.

Several synthetic methods are known for the production of racemic acid (dl-tartaric acid) from maleic acid by the catalytic hydroxylation with hydrogen peroxide.

Thus free maleic acid is reacted in aqueous solution with hydrogen peroxide in the presence of alkali tungstates or molybdates, the intermediate epoxysuccinic acid formed hydrolyzed by boiling and then the racemic acid formed crystallized out of the hydrolysis solution, see Church and Blumberg, "Ind. Eng. Chem.", Vol. 43 (8) pages 1780 to 1786. The mother liquor of the racemic acid crystallization is again returned into the reaction step.

The return or working up of the mother liquor after the crystallization is of decisive significance for the industrial efficiency of the synthetic production of racemic acid, since it contains the added tungstate or molybdate catalyst and besides has a high portion of maleic acid, which cannot be thrown away. It is known to preferably so operate the pictured process that about 60% of the added maleic is reacted (loc. cit.).

The return of the resulting mother liquor, however, has great disadvantages since to begin with in its recycling impurities can become more concentrated which impair the quality of the racemic acid to be recovered.

On the other hand, it has been established that in the return of the mother liquor the speed of epoxidation is greatly reduced because of the saturation in tartaric acid, see Marechal German Offenlegungsschrift No. 2,016,668. The tartaric acid returned with the mother liquor besides is irreversibly oxidized in the epoxidation by hydrogen peroxide to worthless decomposition products such as formic acid, carbonic acid and water, see German Offenlegungsschrift No. 2,016,668.

To be sure according to the process of Marechal it was attempted to avoid a part of the described disadvantages by precipitating the tartaric acid in the mother liquor as the potassium or calcium salt before recycling the mother liquor.

It has been found, however, that the calcium salt is recovered in a form not completely free of tungsten, entirely apart from the fact that the tartaric acid in part can only be recovered with difficulty from its salts. Also the tungsten catalyst after several processing cycles must be precipitated as the calcium salt and recovered therefrom because otherwise its activity subsides.

The racemic acid obtained according to the named process besides is not pure enough for food purposes.

If synthetic racemic acid is to be added in place of natural tartaric acid in the food sector there must be fulfilled very high purity requirements in regard to the content of maleic acid and fumaric acid as well as in regard to the content of traces of heavy metals, i.e., in regard to the tungstate or molybdate content.

Since the described process operates partially with an excess of maleic acid (see Church and Blumberg, loc. cit. and Marechal German O.S. No. 2,016,668), the racemic acid must be crystallized from a maleic acid rich solution and is contaminated by adhering maleic acid, the more so the higher the yield that is crystallized out.

Besides under the reaction conditions maleic acid is partly rearranged to fumaric acid, which because of its lower solubility crystallizes out with the racemic acid. This contaminates the racemic acid and can only be separated therefrom with difficulty.

Consequently the resulting racemic acid in the known processes must be crystallized from solutions which still contain the total catalyst. Thereby a complete separation of the catalyst is not possible since, particularly with tungsten, the tungstic acid readily adheres to the crystallizing racemic acid and this is contaminated up to a blue coloration.

According to Wagner German O.S. No. 1,643,891 and the related Wagner U.S. Pat. No. 3,769,339, it is known to avoid a part of the described disadvantages by producing calcium tartrate by catalyzed reaction of the acidic calcium maleate with hydrogen peroxide. However, it is difficult to set free racemic acid from calcium tartrate, for example, by reaction with sulfuric acid as in the case with natural tartaric acid. The solubility products of the calcium sulfate and calcium tartrate resulting thereby are not sufficiently different so that losses occur through the tartrate content of the calcium sulfate or, in using an excess of sulfuric acid, the tartaric acid must be recovered from a sulfuric acid containing solution, which causes additional problems.

It was not known previously to produce mesotartaric from maleic acid and hydrogen peroxide in the presence of tungstate, i.e., by way of cis-epoxysuccinic acid, but instead mesotartaric acid was recovered for example only in the hydrolysis of trans-epoxysuccinic acid, see Kuhn and Ebel, Berichte 58B, pages 919 et seq. (1925).

The object of the present invention is the production of racemic acid in higher yield and purity, especially of food grade purity, as well as of mesotartaric acid with simultaneous recovery of the catalyst.

It has now been found that racemic acid can be recovered in a continuously or discontinuously operated process in higher yields and in very pure condition in addition to mesotartaric acid in the reaction of alkali metal maleate with aqueous hydrogen peroxide in the presence of alkali tungstate if the molar ratio of hydrogen peroxide to maleic acid is greater than 1:1 and the alkali salt of cis-epoxysuccinic acid formed together with the alkali tungstate, in a given case after destroying the excess hydrogen peroxide, are converted to free cis-epoxysuccinic acid and free tungstic acid by leading them over a strongly acidic cation exchanger, e.g., a strong cation exchange resin, whereupon the hydrolysis of the free cis-epoxysuccinic acid to racemic acid and mesotartaric acid can take place either in the presence or the absence of the free tungstic acid, whereby the tungstic acid in the case of catalyst free hydrolysis before, and in the case of catalyst containing hydrolysis after this hydrolysis is removed with an anion exchanger, e.g., an anion exchanger resin, and the racemic acid is then in known manner crystallized out of the tungstic acid free hydrolysis mixture by lowering the temperature, in a given case by evaporation of water, whereupon the mesotartaric acid remains in the mother liquor and there is recovered from the mother liquor either by crystallization or evaporation to dryness, in a given case in admixture with racemic acid, unreacted cis-epoxysuccinic acid and maleic acid, while the anion exchanger laden with the tungstic acid is regenerated in known manner with dilute aqueous alkali and, in a given case, the resulting solution of alkali tungstate, eventually after treatment with activated carbon is returned directly into the epoxidation.

According to the process of the invention, dl-tartaric acid is for the first time industrially crystallized out of a solution which is practically free from tungstic acid and, to an extraordinarily small residue, is free from maleic acid and can therefrom be recovered from this solution in food grade purity.

Further for the first time, it was observed that in the hydrolysis of the cis-epoxysuccinic acid mesotartaric acid was formed, and it was found that its portion is influenced by the type of carrying out the hydrolysis, i.e., by the presence or absence of the tungstate catalyst.

The object of the invention is attained by the combination of the individual steps of the invention, i.e., proceeding from the salts of the maleic acid, which are reacted with excess hydrogen peroxide in the presence of tungstate, by way of the recovery of the free cis-epoxysuccinic acid and free tungstic acid with cation exchangers, as well as the described types of the hydrolysis and the removal of the tungstic acid by anion exchangers, the working up of the solution through fractional crystallization, dl-tartaric acid of high purity is produced and the resulting mesotartaric acid is recovered.

The tungstate catalyst is recovered very simply and practically quantitatively and without cumbersome working up returned directly in aqueous solution into the epoxidation step.

Furthermore, the process of the invention is easy to carry out industrially since up to the crystallization of the tartaric acid working is only with aqueous solutions and the known difficult manipulations of solids are completely avoided.

As alkali maleates or alkali tungstates, there can be used the sodium, potassium and ammonium compounds, preferably the sodium compounds. (As used herein, the term alkali includes the Group Ia metals and ammonium.) The amounts of alkali maleate added are so regulated that the reaction runs in homogeneous medium during the entire duration of the reaction. Preferably in using sodium maleate the reaction solution should contain 10 to 20 weight % maleic acid.

The ratio of hydrogen peroxide to maleic acid added should be between 1.01 to 5:1, preferably between 1.1 to 2:1. Especially favorable is a ratio of 1.1 to 1.3:1. The starting concentration of the aqueous $H_2O_2$ solution is immaterial. Thereby the excess of hydrogen peroxide should be so regulated that even with the descomposition losses of hydrogen peroxide there is always present during the entire reaction an excess of hydrogen peroxide in relation to maleic acid.

The reaction is usually carried out at pH values between 3 and 5.5, preferably at pH values of 4 to 5 and at temperatures of 70° to 90° C., although higher temperatures up to the boiling limit of the aqueous solution and lower temperatures down to the solubility limit of the maleate added or the epoxysuccinate formed by the reaction can be used.

The catalyst, i.e., the alkali tungstate, e.g., sodium tungstate, potassium tungstate or ammonium tungstate, can be used in amounts of 0.5 to 5 mol %, preferably 1 to 2 mol %, based on the maleic acid employed.

Thereby the reaction of the sodium salts of maleic acid with hydrogen peroxide in the presence of sodium tungstate to the sodium salts of the cis-epoxysuccinic acid is also known in itself, see Payne et al, J. Org. Chem., Vol. 24 (1959), pages 54 et seq., however, their change corresponding to the further steps of the process of the invention to produce tartaric acid are new.

The alkali maleate according to the process of the invention can be added either in preformed form or can be formed in situ in the reactor, and as starting material there can be used either maleic acid or maleic anhyride.

After the epoxidation reaction, the hydrogen peroxide and other peroxygen compounds such as pertungstates in a given case if necessary are removed. For removal of the peroxygen compounds there can be called upon both known chemical reactions as well as the known metal catalyzed decomposition of these compounds. Advantageously one works so that the solution is not contaminated and uses a catalyst which contains platinum on a solid carrier, for example, 0.01 to 5 weight % platinum on chemically inert low pore carriers which consist of more than 90% $SiO_2$, preferably 0.05 to 0.5 weight % platinum. With these catalysts, the peroxygen compounds in the solutions in question can be destroyed at normal pressure at temperatures of 20°–100° C., preferably at 60°–80° C.

Figure 2:
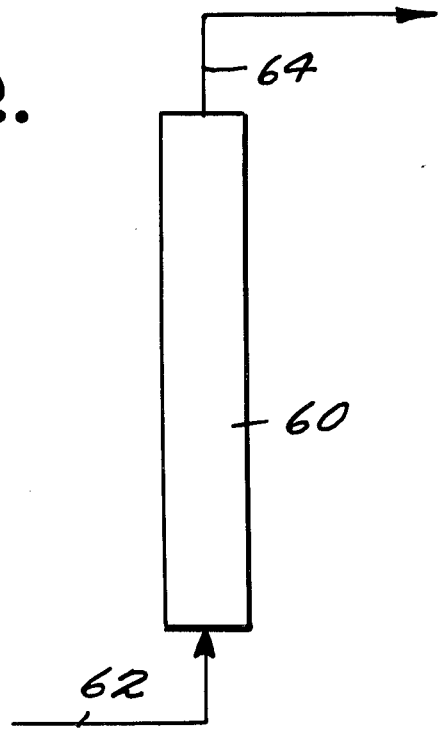

The invention will be understood best in connection with the drawings wherein:

FIG. 1 is a diagrammatic illustration of a particularly preferred form of the first aspect of the invention up to the step of peroxygen decomposition; and FIG. 2 is a diagrammatic illustration of the second aspect of the invention which will be described hereinafter.

Referring more specifically to FIG. 1 in a continuously operated circulatory reactor 1, which works as an ideal agitator vessel with complete backmixing of the solution held at constant temperature by a heat exchanger, there was fed an aqueous solution of hydrogen peroxide and maleic acid through line 17 and an aqueous solution of sodium tungstate and sodium hydroxide via line 18. The solution ran from reaction 1 via line 52 into a similarly equipped reactor 2 in which, in case it is necessary, additional aqueous sodium hydroxide can be closed in via line 20 in order to maintain a fixed pH value. The oxygen formed by decomposition of hydrogen peroxide escapes via lines 19 and 21.

The reaction mixture leaving reactor 2 is conversed via line 22 into a subsequent reaction zone 3 built as a flow tube, out of which the reacted mixture is led via line 23 into the bottom of a column 4 filled with the decomposition catalyst. The oxygen formed by the decomposition leaves column 4 via line 24 while the solution runs via line 25 into an intermediate container 5 in which it must be held at a temperature above the crystallization temperature of the dissolved solids.

To recover the free cis-epoxysuccinic acid there can be used as strongly acidic cation exchangers all of the commercial types, especially those based on polystyrene or styrene-divinylbenzene copolymers having acid groups, preferably free sulfonic acid groups, attached thereto. Thus there can be used any of the particulate strongly acidic cation exchange resins in the Encyclopedia of Polymer Science and Technology, Vol. 7, pages 692–742. The entire disclosure of said pages is hereby incorporated by reference and relied upon.

For the process of the invention, it is immaterial whether there are employed known parallel flow, countercurrent flow or continuous ion-exchange processes. However, it is advantageous, without the process being limited thereby, to carry out the regeneration of the cation exchange resin countercurrently to the loading. Therethrough there are obtained the known advantages of countercurrent processes such as less alkali slippage (slippage = residual content of alkali in the exchanged solution) and less requirement of regeneration agent and therewith its higher economy is utilized. Particularly favorable are processes in which there are avoided the too strong dilution of the exchanged solution by the wash water accumulating in the course of the regeneration, since this dilution water additionally must be evaporated in the later working up.

An especially preferred form for recovery of the cis-epoxysuccinic acid by ion exchange will likewise be explained in connection with FIG. 1.

The solution present in container 5 goes via line 26 at a temperature above the crystallization temperature into the bottom of column 6 filled with a cation exchange resin and from there is led via line 54 into a similar column 7 operating as a complete purification. An aqueous solution of epoxysuccinic acid and tungstic acid runs out of the top of column 7 via line 27. Thereby column 6 is operated preferably up to break through the alkali whereupon the line 26 is reversed to column 7 and a fresh regenerated column 8 serves as complete purification. Column 6 then is regenerated. With corresponding continuation of this procedure a quasi continuous flow can be attained.

Thereby it has proven advantageous to so dimension the ion exchange bed that to operate below a flow velocity at which the resin is suspended or fluidized which would impair the exchange. In this method of operation additional industrial apparatus is not necessary for operation of countercurrent filters, see in this connection K. Dorfner, Ionenaustauscher, Walter de Gruyter & Co., Berlin (1970).

The described method of operation has proven particularly simple to carry out since above all the reactions in the reactors 1, 2, 3 and 4 fix the concentration and flow per hour of the exchanging solution over the cation exchange column so that higher flows per hour which cause suspensions and reduce the effectiveness of the exchanger are not necessary.

Furthermore FIG. 1 explains the washing of an exhausted ion exchange column and its regeneration with reference to column 8.

Thereby this method has proven particularly advantageous in regard to the saving of wash water and the avoidance of too strong dilution of the product solution with only slight loss of product. The process of this type can be carried out so that a subsequent solution drives out that present on the column. Or else the column is drained before delivery of a new solution. It must merely be guaranteed that the regenerating acid is not mixed with the product stream.

Thereby first the contents of column 8 are led back to container 5 via line 28, container 9 and line 29 and subsequently column 8 washed with preconcentrated wash water from container 10 and line 31. The discharge from the column likewise goes back via line 28 and container 9 as well as line 29 to container 5. Thereupon it is washed with distilled water via line 32. This discharge is led into container 10 via line 28, container 9 and line 30 and used again in the next cycle.

The subsequent regeneration with after washing can be carried out in known manner, for example, with dilute hydrochloric acid, according to the specifications of the resin manufacturer via lines 33 and 35. Thereby it is advantageous to draw off the last wash water and to load the empty column in order to avoid unnecessary dilution of the product.

The aqueous solution of epoxysuccinic acid and tungstic acid leaving the cation exchanger, which contains besides small amounts of unreacted maleic acid and small amounts of tartaric acid is then reacted to tartaric acid at temperatures of 50°-200° C., preferably at temperatures of 100°-150° C.

Hereby one can proceed once so that the solution going via line 27 to container 11 is boiled under reflux, for example, for 5 hours, in that container.

However, one can also proceed so that the solution from line 27 at temperatures from about 20°-95° C., these temperatures are only limited by the stability of the anion exchanger, e.g., an anion exchange resin, is led via lines 37, 38 and 56 to the anion exchangers 13 and 14, whereupon the solution of the epoxysuccinic acid free of tungstic acid then flowing out via line 40 is hydrolyzed. The hydrolysis of aqueous cis-epoxysuccinic acid solutions is known in itself, see R. Kuhn and F. Ebel, Ber. 58B, 919 et seq. (1925); G. Wode, Svensk Kem. Tids., Vol. 40, pages 221 et seq. (1928) and Chem. Abst., Vol. 23 (1929) page 2344 as well as Yonemitsu, German Offenlegungsschrift 2,400,767.

Surprisingly, it was established that the portion of unexpectedly formed mesotartaric acid in the hydrolysis of the cis-epoxysuccinic acid is dependent of whether the hydrolysis is carried out before or after the anion exchange. This is the more surprising since according to R. Kuhn et al (loc. cit.) and Yonemitsu German O.S. 2,400,767 in the hydrolysis of an aqueous solution of cis-epoxysuccinic acid, as that resulting after the anion exchanger in the process of the invention, only d,l-tartaric acid forms. However, according to the process of this invention it was found that the portion of meso-tartaric acid formed can be reduced considerably if the hydrolysis is carried out in the presence of 0.1-5 mol %, preferably 1-2 mol %, of tungstic acid based on the cis-epoxysuccinic acid, i.e., before the anion exchange, in this regard see examples 4 and 5.

It is also possible according to the process of the invention to so regulate the conditions according to demand more or less mesotartaric acid is formed. Depending on demand also there can be obtained more or less dl-tartaric acid and in cases in which dl-tartaric is not in demand or has insufficient demand it can be replaced or supplemented by meso-tartaric acid.

For example this is the case if the solubility of the dl-tartaric acid is not adequate for the determined purposes of use. Since dl-tartaric acid differs from natural tartaric acid in its substantially poorer solubility while the solubility of mesotartaric acid is in the neighborhood of natural tartaric acid, then a solution with a higher portion of mesotartaric acid can also always be produced if the solubility of dl-tartaric acid is not sufficient for the concerned purpose of an industrial region of use, as for example in the construction industry or in the electroplating industry.

The introduction of anion exchangers for the removal of tungsten containing compounds, even in the presence of polybasic complex forming acids, such as citric acid is known in itself (see, D. Shishkov, E. Koleva, Doklady, Bolg. Akad. Nauk, Vol. 17 (10) pages 909–912 (1964) and Chemisches Zeutralblatt (1966) 27–538). In a second aspect of this invention is shown that in general there exists a possibility for purification of synthetic racemic acid solutions by conducting them over anion exchangers.

As anion exchangers there can be employed all commercial types, preferably weakly basic anion exchangers based on polystyrene or styrene-divinyl benzene copolymer with a macroporous structure and an amino function as the exchange active groups. Thus there can be used the particulate anion exchange resins mentioned in the aforecited Encyclopedia of Polymer Science and Technology, Vol. 7, pages 692–742. Also there can be used the anion exchange resins mentioned in Kioustelidis German O.S. No. 2,140,055 such as Amberlite IR 4B and Duolite A7, for example.

In the here described process of the invention it is immaterial whether the anion exchange is carried out according to a known parallel flow, countercurrent flow or continous ion exchange process. This exchange process is also prepared as shown in FIG. 1, namely in the columns 12, 13 and 14, which can be connected as correspondingly described for the cation exchangers in columns 6, 7 and 8.

Accordingly, there are installed 3 columns which can be charged from below countercurrently for regeneration and of which two are connected in succession, while the third is in the regeneration.

The first column is operated preferably up to the break through of tungsten, while the second freshly regenerated column serves as complete purification.

Thereby in deviation from the cation exchange there must be used one of the countercurrent techniques, for example, the suspended bed process, see K. Dorfner, loc. cit.

Regeneration and washing of an exhausted column is explained with reference to column 12 and FIG. 1, namely the most preferred form of the invention.

First, the contents of column 12 are displaced with distilled water via line 47 and returned via lines 39 and 38 for insertion into the anion exchanger 13 or 14. Thereby the least possible water is used in order not to dilute the product unnecessarily. Generally 1–5 bed volumes of water are sufficient. The anion exchange beds are then regenerated, as recommended by the resin manufacturers, with dilute aqueous sodium hydroxide supplied via lines 48 and 49 and washed free of alkali with water. The regenerate running out via line 50 contains besides small amounts of tartaric acid, epoxysuccinic acid and maleic acid or their sodium salts the tungstate catalyst which can be returned to the reaction step practically quantitatively as a dilute, aqueous solution and can serve, for example, for preparation of the mixture in line 18.

It is thereby necessary to insert in columns 12, 13 and 14 at least sufficient anion exchange resin that from the capacity of the resin inserted there only has to result so seldom the regeneration and washing of an anion exchange column that there can be used the amount of water—fed with the wash water and dilute sodium hydroxide and returned via line 50—for the preparing of the solutions for the reactors 1 and 2, which are introduced via lines 17, 18 and 20.

Preferably before reintroduction of the regenerate in line 50 it is treated with activated carbon, since occasionally in the continuous running of the process yellow brown impurities are adsorbed on the anion exchanger. These reach the regenerate in line 50 in the regeneration of the resin and contaminate the regenerate.

One can proceed in the purification so that 0.05–1 weight %, preferably 0.1–1.4 weigth % of activated carbon based on the solution is stirred in, preferably at room temperature.

After a time of 5 minutes to 5 hours the activated carbon is filtered off and the completely uncolored solution used again. In place of room temperature higher or lower temperatures also can be employed, besides other processes can be used in place of the stirring in process, for example column processes in which the colored solution is led over an activated carbon tower.

The solution present in line 40 after hydrolysis and anion exchange, which is practically free from tungstic acid, and besides small amounts of unreacted or on the anion exchange resin not separated maleic acid or traces of fumaric acid, contains the total dl-tartaric acid as well as a corresponding portion of mesotartaric acid and, in a given case, unreacted epoxysuccinic acid, can then be worked up, see Church and Blumberg, loc. cit. In a given case after evaporation of water the solution is cooled, the racemic acid filtered off and washed with cold water and subsequently dried.

The mesotartaric acid can thereby, for example after evaporation to dryness, be recovered in admixture with non-crystallized racemic acid and the residue of maleic acid and cis-epoxysuccinic acid.

The evaporation is best carried out at temperatures between 40° and 150° C., preferably 60°–110° C. and the crystallization at temperatures of 1°–25° C.

In order to produce particularly pure racemic acid, the solution is best fractionally crystallized.

For this purpose in a preferred form of the process, see FIG. 1, the solution is led for example from line 40 to a circulation evaporator 15 in which a portion of the water is distilled off under vacuum or pressure via line 41.

This amount of water is adjusted according to the concentration of the solution of racemic acid, mesotartaric acid, cis-epoxysuccinic acid and maleic acid coming from the anion exchanger and according to the degree of purity of the racemic acid which it is desired to produce. The concentrated solution is led via line 43 to a crystallization and filtration stage 16 so that first crystallized racemic acid can be recovered in line 45 and the aqueous mother liquor (called Mula I below) can be recovered in line 46. The lines 42 and 44 merely serve for ventilation or maintaining the desired pressure.

The thus obtained Mula I can now again be evaporated in a corresponding manner to a further racemic acid fraction which can have a lesser purity according to the solubility and concentration of the remaining constituents. The number of fractions thereby is selectable at random. However, it is convenient to crystallize in not more than 24 fractions and to evaporate the final mother liquor to dryness.

In the working up of the last mother liquor, it has been found that it best contains the least possible cise-poxysuccinic acid, since this crystallizes poorly and inclines to stick and thus make difficult the working up. Since, however, even at high reaction during the hydrolysis of 98–99%, cis-epoxysuccinic acid clearly concentrates in the mother liquor, it is industrially particularly advantageous to operate the evaporation under conditions in which the hydrolysis of the epoxysuccinic acid is continued, see example 2, to avoid too long reaction times in the true hydrolysis in container 11.

Advantageous for example a mother liquor can also undergo a subsequent saponification, see example 3, since in this place the total volume of the solution is clearly lower than with the hydrolysis in container 11 and therefore a smaller container is necessary.

The industrial advantage of the first aspect of the invention, as already said, is first in the recovery of racemic acid which is very pure in reference to maleic acid, fumaric acid and impurities from the catalyst.

According to the "Deutschen Arzneimittelbuch 7" (German Medicine Book 7) for tartaric acid there is permitted a maximum heavy metal content (calculated as lead) of 20 ppm. The tungsten content of the dl-tartaric acid obtained according to the process of the invention is less than 5 ppm. According to the American Food Chemical Code of 1966 malic acid in the food grade range and produced from maleic acid is allowed to contain maximally 0.05 weight % maleic acid and 0.7 weight % fumaric acid.

The dl-tartaric acid recovered by the process of the invention already contains less than 0.02 weight % of maleic acid and fumaric acid and has therefore food grade purity.

Beside the process of the invention, as previously stated, is easy to carry out industrially, since up to the crystallization of the tartaric acid one is only working with aqueous solutions. The recovered catalyst can besides be returned immediately into the reaction step.

Unless otherwise indicated, all parts and percentages are by weight.

EXAMPLE 1

The process was carried out in an apparatus corresponding to FIG. 1 and the subsequent data is in reference to a continuous operation after reaching stationary conditions.

There were fed into reactor 1 via line 17 820 g/hour of an aqueous solution of 2.27 mol/h of maleic acid and 2.76 mol/h of $H_2O_2$, via line 18 an aqueous solution of 830 g/h containing 3.6 mol/h NaOH and 0.0352 mol/h $Na_2WO_4$, as well as small amounts of an acid mixture returned via line 50; in reactor 2 there were additionally added via line 20 0.395 mol/h NaOH in 80 g/h of an aqueous solution. Reactors 1, 2 and 3 were operated at about 80° C., the operating volume of reactor 1 was 1650 ml, that of reactor 2 1280 ml, the subsequent reaction zone 3 consists of a 5.40 meter long tube (diameter 38 mm) which is filled with 4 mm Raschig rings.

Column 4 is operated at about 80° C. and consists of a tube (38 mm diameter) that is filled with 1100 ml of a catalyst which contains 0.1% platinum on a chemically inert, low pore carrier, which consists of more than 90 weight % silicon dioxide and whose pentich sizes range between 3-5 mm.

The residual content of $H_2O_2$ in the amount flowing in line 23 is about 0.6%; after leaving the decomposition catalyst the hydrogen peroxide is practically quantitatively destroyed in line 25. Via line 25 there flows about 1720 g/h of an aqueous solution in which are contained in the form of their sodium salts besides cis-epoxysuccinic acid about 0.011 mol/h of maleic acid and 0.25 mol/h of tartaric acid into the intermediate container 5 which is held at a temperature of 40° C. The solution is conveyed via line 26 heated to about 40° C. into the cation exchangers 6 and 7. The diameter of the exchange columns were 10 cm; they are filled with about 11 liters of a cation exchanger based on a styrene polymer containing free sulfonic acid groups (i.e. a sulfonated styrene-divinyl benzene resin ®Lewatit S100LF; Bayer, Leverkusen) and some inert resin. Thereby the cation exchange resin in the swollen condition fills up about 95% of the free space between 2 sieve trays.

Column 6 at the beginning of a charging cycle is filled with product; column 7 after the regeneration empty. Corresponding to the supply via lines 25 and 29 there is conveyed away from container 5 solution with a constant flow averaging 3500-4000 g/h. As soon as sodium ions begin to break through at the top of column 6 stream 26 is connected to column 7 from which it is conveyed out into the ready, regenerated column 8.

The washing and regeneration of an exhausted column is explained in connection with column 8. First column 8 is emptied, via line 28 into container 9 from which the contents return to container 5 via line 29. Subsequently column 8 is washed with preconcentrated wash water held in container 10; the wash water running through is likewise returned via container 9 back to 5.

Accordingly column 8 is washed with 4.5 kg of completely desalted water which is returned via line 28, container 9 and line 30 into container 10. Subsequently the column is regenerated via line 33 with 13.5 kg of 6.5 weight % hydrochloric acid and then washed with 15 liters of completely desalted water. The washing and regeneration process must be repeated on the average every 4.5-5 hours.

There flows via line 27 on the average about 2700 g/h of an aqueous solution of cis-epoxysuccinic acid which contains 11 mol % of tartaric acid based on the total acid, traces of maleic acid and the entire tungstic acid in a concentration of 0.84 mol/1000 g of solution of dibasic acid to container 11. Thereby through the washing process of the cation exchanger there was only a dilution to about 64% of the starting concentration with losses which amounted to about 0.5% of that inserted. In container 11 the solution was boiled for 5 hours at about 100° C. under reflux; in order to carry out the further running continuously a second container (not shown) is operated parallel in reversed hookup.

After ending the hydrolysis after cooling to room temperature there was led from below over the anion exchange columns 13 and 14 connected in series 2700 g/h of an aqueous solution containing 2.03 mol/h racemic acid, 0.13 mol/h mesotartaric acid, 0.06 mol/h cis-epoxysuccinic acid and 0.01 mol/h maleic acid as well as all of the tungsten catalyst.

As anion exchangers there were used 3 columns having internal diameters of 43 mm. About 1.3 liters of a macroporous, monofunctional weakly basic anion exchange resin based on a styrene polymer (styrene-divinyl benzene copolymer, ®Lewatit MP62GA; Bayer, Leverkusen) were filled into each column and in the unloaded condition occupied about 60% of the space between 2 sieve trays.

The anion exchange was carried out according to the suspended bed process. After every 24 hours a column at the break through of tungsten was regenerated according to the previous description of this step of the invention and connected as the fine purification column behind the column connected up to the reversal point as a fine purification column.

The washing and regenerating process are described in connection with column 12. First the column contents are displaced with 3.5 kg of completely desalted water via line 47 and the contents returned via lines 39/38 to column 13. According to the direction of the resin manufacturers, the solution was first regenerated with 3.2 kg of 4 weight % sodium hydroxide from lines 48 and 49 and subsequently washed alkali free with 5.2 of completely desalted water; to avoid dilution of the product the water level was always held only a little over the resin.

To remove a yellow coloration, the aqueous regenerate was treated about 30 minutes with 0.2 pulverized activated carbon, this filtered off and the solution returned again via line 50 for insertion in reactor 1.

Via line 40 there flowed a periodic average of 2.23 mol/h of dibasic acids and about 2500 g/h of water and this solution was conveyed to a circulation evaporator 15 in which about 1400 ml of water per hour was evaporated off via line 41 while operating at a temperature of 80° C. The thus concentrated solution was discontinuously cooled to about 5° C. in a stirring container (not shown). The racemic acid crystallized out was filtered off and washed twice with 10 weight % of cold, distilled water, based on the solid material.

There were obtained, calculated as grams per hours, after drying, 209 g/h (i.e. 61.5% based on the maleic acid) of racemic acid which contained a maximum of 2-3 ppm of tungsten and less than 0.02 maleic acid and fumaric acid.

In about 1200 g/h of the mother liquor of this first evaporation step there are still present 96 grams of racemic acid, 19.5 grams of mesotartaric acid, 7.9 grams of cis-epoxysuccinic acid and 1.1 grams of maleic acid.

After evaporation of about 800 ml/h of water at about 80° C., subsequent crystallization at about 5° C. and washing with cold water -as with the first crystallization- there were obtained after drying, 74 g/h dl-tartaric acid (21.6% based on the maleic acid) which contained about 0.02-0.03% maleic acid, less than 0.02% fumaric acid and less than 5 ppm tungsten.

The mesotartaric acid fraction of 15.1% based on the maleic acid, can be recovered by evaporation to dryness. It contains 38.5 weight % mesotartaric acid, besides 43.5 weight % racemic acid, 15.6 weight % epoxysuccinic acid and 2.4 weight % maleic acid.

The mixture is industrially usable as such but it can also be purified by further fractional crystallizations and the racemic acid can be even more completely separated.

From the regenerate of the anion exchanger in line 50 there result in every 24 hours, 8.9 kg of a solution which contains 247.7 g of sodium tungstate which are 99.75% of that added, and small amounts of the sodium salts of the acids appearing in the reaction. This solution, replenished with aqueous sodium hydroxide, water and very small amount of sodium tungstate, yields a mixture that is directly carried into the reaction stage via line 18.

EXAMPLE 2

A flow of 2500 g/h of water and an average of 2.23 mol/hr of dibasic acid is drawn off via line 40 as explained in example 1, however, it is then led to a circulation evaporator having an operating content of 1950 ml, in which about 1400 ml/hr. of water is evaporated under pressure at 112° C. boiling temperature. The working up took place in the manner described in example 1. There was crystallized 62.5% racemic acid based on the maleic acid of corresponding purity. After the second evaporation and crystallization which were carried out as in example 1 there was obtained 22% of racemic acid of similar purity to that in example 1 and after evaporation to dryness there was obtained a mixture of mesotartaric acid (6%), racemic acid (6%), maleic acid (0.5%) and epoxysuccinic acid (0.3%), in each case based on the maleic acid employed.

In contrast to example 1 in which a mesotartaric acid fraction with 15.6 weight % epoxysuccinic acid is obtained, there is obtained in this case only 2.1% epoxysuccinic acid, the difference being converted into racemic acid and mesotartaric acid. Besides such a slightly adhesive product was obtained that the working up was facilitated.

EXAMPLE 3

In order to improve the reaction in reference to epoxysuccinic acid a subsequent hydrolysis of the mother liquor of the second crystallization is carried out as shown in the following.

One liter of mother liquor of the second crystallization according to example 1 was boiled in a glass flask for 5 hours under reflux. The solution contained 1.01 mol/1000 g of a mixture of dibasic acids which was composed of 15.5 mol % maleic acid, 35 mol % racemic acid, 37 mol % mesotartaric acid and 12.5% epoxysuccinic acid. After 5 hours of subsequent hydrolysis the solution contained 14.5 mol % maleic acid, 42 mol % racemic acid, 39 mol % mesotartaric acid, 1 mol % fumaric acid and about 3.5 mol % epoxysuccinic acid.

The reaction in the subseqent hydrolysis based on epoxysuccinic acid amounted to 72% whereby additional racemic acid and mesotartaric acid were formed.

EXAMPLE 4

A solution which was obtained via line 27 according to example 1 was not hydrolyzed, but first was led over an anion exchanger, as is generally described in example 1.

The solution contained 0.97 mol/1000 g of a mixture of dibasic acids, namely 0.20 mol/1000 g tartaric acid and 0.75 mol/1000 g epoxysuccinic acid. The tungsten content of the solution was below 2 ppm (not detectable). After hydrolysis at 95° C. there resulted, based on the starting content of epoxysuccinic acid and tartaric acid, the following product distribution.

| Minutes | Mol % dl-tartaric Acid | Mesotartaric Acid | Epoxysuccinic Acid | Selectivity of Mesotartaric Acid Related to the Formed Tartaric Acid |
|---|---|---|---|---|
| 210 | 59 | 9 | 32 | 13.2 |
| 285 | 65 | 11 | 24 | 14.5 |
| 403 | 70 | 14 | 16 | 16.7 |
| 1,390 | 83 | 17 | (<0.5) | 17 |

According to the process described in example 1 there was attained a selectivity of 6% mesotartaric acid based on the tartaric acid formed at a 97% reaction of epoxysuccinic acid. The analysis data obtained in example 4 was determined with the help of the nuclear resonance method.

EXAMPLE 5

Three hundred grams of a solution which contained 1.31 mol/1000 g of dibasic acids and was produced in an analogous manner to the product obtained in example 1 via line 27, had a content of 0.013 mol/1000 g of tungstic acid. The solution was boiled in a glass flask for 5 hours under reflux.

Based on the acid added there were obtained in mol percents: 4.3% epoxysuccinic acid, 9.2% mesotartaric acid and 86.4% dl-tartaric acid. The selectivity of mesotartaric acid based on the sum of tartaric acid formed amounted to 9.6%.

The same solution was passed over a weakly basic, macroporous anion exchanger based on styrene-divinyl benzene resin and containing exchange active amino groups (®Lewatit MP62; Bayer, Leverkusen) and contained after the exchange less than 2 ppm of tungsten. The acid concentration was 1.335 mol of dibasic acid/1000 g of solution. Three hundred g of the solution was boiled under reflux for 5 hours. After working up there were obtained in mol percents 64.1% dl-tartaric acid, 17.2% mesotartaric acid and 18.3% epoxysuccinic acid from the acid inserted. The selectivity of mesotartaric acid was 21.2% based on the tartaric acid formed.

The analysis results of example 5 were obtained by fractional crystallization after evaporation and identification of the fractions.

The second aspect of the invention relates to the separation of maleic acid from synthetic tartaric acid.

As previously pointed out according to a known process for the production of tartaric acid there is hydroxylyzed maleic acid with the help of hydrogen peroxide in the presence of tungstic acid or molybdic acid as catalyst and the racemic acid formed then recovered by crystallization, see Church et al. and German O.S. No. 2,016,668, supra. Since only about 60% of the maleic acid added is reacted, the tartaric acid formed must be crystallized from and aqueous solution having a high maleic acid content.

Because of the solubility ratio tartaric acid crystallizes out and maleic acid for the most part remains in the solution. However, the separation of the maleic acid was more incomplete, i.e., tartaric acid obtained was more strongly contaminated by adhering maleic acid the more complete the tartaric acid should be recovered from the solution by crystallization. The same is true also when using excess maleic acid before the reaction begins: the more of this excess, the more contaminated was the tartaric acid.

Also in these known processes tartaric acid was crystallized out of solutions which still contained the catalyst, such as tungstic acid or molybdic acid, see Church et al. and German O.S. No. 2.016,668. These catalysts, however, were only separated off with great difficulty by crystallization of the tartaric acid, since the tartaric acid has the maleic acid adhering thereto and at higher proportions is even contaminated up to a blue coloration.

The tartaric acid produced from the maleic acid was always more or less strongly contaminated by maleic acid or catalysts acid or both simultaneously.

Natural tartaric acid is used in large amounts in foods, for example as an acid agent or taste improver. Synthetically produced tartaric acid can be used if it is pure enough, i.e. if it has a sufficiently high degree of purity in reference to the maleic acid and catalyst contents as pointed out above.

The object of the invention therefore is the separation of maleic or maleic acid together with catalysts such a tungstic acid or molybdic acid from synthetic tartaric acid produced in any manner.

It has now been found that maleic acid can be separated from maleic acid containing synthetic tartaric acid if an aqueous solution of crude tartaric acid which can also still contain the catalyst employed, e.g. molybdic acid of tungstic acid, is led over a basic anion exchanger which is present in the hydroxyl or tartrate form. In this process racemic acid, D-, L- and mesotartaric acid are called "tartaric acid".

Previously those in the art believed that only the metal catalyst could be separated from an aqueous solution or organic acid with the help of anion exchangers, see D. Shishkov in Doklady Bolgerskoj, Akad. Nauk cited supra; Chemisches teutrelblatt 1966, 27–538 as well as German O.S. No. 2,140,055, but the maleic acid must be washed out of the tartaric acid formed. However, thereby considerable amounts of tartaric acid again go into solution and the yield is correspondingly less.

However, it has been found by the process of the invention that the named anion exchangers are in position to separate maleic acid from the tartaric acid containing solution and that in separating the maleic acid there can also be removed simultaneously the entire catalyst, if molybdic acid, tungstic acid or both are present. Since the crystallization then takes place out of an almost pure solution, the expense of washing is greatly reduced.

It could not be predicted that maleic acid could be separated from racemic acid by anion exchangers since the selectivity of iron exchangers is known to be dependent upon the type of ions exchanged, i.e. from their size, charge and the basicity of the acid-anion to be exchanged, see K. Dorfner, Ionenaustauscher, supra.

Precisely in regard to these properties, however, maleic acid and tartaric acid are vert similar; moreover the dissociation constants of the two acids are very close.

Surprisingly, however, the binding capacity of the named anion exchangers is so large that even at a large excess of racemic acid there can be separated maleic acid, see example 6, although the known tartaric acid itself is bound from anion exchangers from aqueous solution, see Matchett, Ind. Eng. Chem., Vol. 36, pages 851–857 (1944).

As anion exchangers there can be used any of those mentioned previously, preferably weakly basic anion exchangers based on polystyrene or styrene-divinyl benzene with a macroporous structure and an amino function as the exchange active groups.

The temperature at which the exchange is undertaken is only limited by the temperature resistance of the resin and the boiling temperature of the solution. However, the temperature is preferably held at 20° to 50° C.

The upper limit on the concentration of the aqueous solution is only limited by the solubility of the dissolved constituents, especially of the tartaric acid and at a customary working temperature of about 25° C., preferably at 10 to 20 weight %, based on the tartaric acid.

The process of the invention is preferably suitable for the separation of maleic acid or a mixture of maleic acid and the catalyst acids if these impurities are present in concentrations up to 5 mol % based on the tartaric acid. The concentration of impurities can be as low as 0.01 mol % based on the tartaric acid. Compositions within such range give the best separation of impurities and the exchanger employed does not have to be frequently regenerated.

The stated concentration range, however, is also the most important commercially.

Instead of completely using up the capacity of the ion exchanger, naturally it is also possible to stop the exchange earlier, e.g. if the maleic acid and catalyst acid concentrations have reached the previously stated values in the solution flowing from the anion exchanger. It is also possible to reach extraordinarily small residual content of impurities in this way, see example 6.

The exhausted ion exchange resin can be regenerated in known manner, e.g. with the aqueous alkali, e.g. sodium hydroxide whereby the bound acids are recovered nearly quantitatively in the form of the aqueous solution of their alkali salts. The regenerate solution can be used again, for example, in the production of racemic acid and mesotartaric acid in the manner described above in connection with FIG. 1 and examples 1–5.

The ion-exchange process, as previously set forth can be carried out in known manner such as parallel flow, countercurrent flow or continuous ion exchange, see K. Dorfner, loc. cit.

EXAMPLE 6

The experiment was carried out in an apparatus shown schematically in FIG. 1. The exchange column 60 had a diameter of 2 cm and was filled with 250 ml of a weakly basic anion exchange resin which previously had been regenerated with 1.5 liters of a 3 weight % aqueous sodium hydroxide solution passed from above and the resin was then washed until neutral. As the resin there was used a macroporous, monofunctional weakly basic anion exchanger having the amino groups connected to a styrene-divinyl benzene resin (®Lewatit MP62GA; Bayer, Leverhusen). The resin was loaded from below via line 62 at 22° C. with a velocity of 750 ml/h according to the suspended bed technique; the exchanged solution was drawn off via line 64. The resin was covered with completely desalted water before beginning the loading.

In the sequence 1, 2, 3 the charged solutions 1, 2, 3 were passed over the column. They contained in aqueous solution about 1 mol/1000 g dl-tartaric acid and maleic acid, whose content was determined polarographically.

| Solution No. | dl-tartaric Acid + Maleic Acid mol/l | Maleic Acid mol/l | Mol % Maleic Acid | Amount Grams |
|---|---|---|---|---|
| 1 | 0.98 | 0.013 | 1.33 | 5000 |
| 2 | 1.06 | 0.026 | 2.45 | 5000 |
| 3 | 0.99 | 0.0245 | 2.48 | 4140 |

(The mol % of maleic acid in the above table refers to the content of maleic acid in mol % based on the total acid content (dl-tartaric acid+maleic acid).)

Fractions were drawn off via line 64 and analyzed as set forth below.

| Withdrawn Fraction No. | dl-tartaric Acid + Maleic Acid mol/l | Maleic Acid mol/l | Mol % Maleic Acid | Amount Grams |
|---|---|---|---|---|
| 4 | 0.20 | not detectable | ~0 | 635 |
| 5 | 0.92 | not detectable | ~0 | 297 |
| 6 | 0.97 | not detectable | ~0 | 1091 |
| 7 | 0.98 | $8.1 \times 10^{-5}$ | 0.0083 | 1052 |
| 8 | 0.98 | $3.0 \times 10^{-4}$ | 0.031 | 1146 |
| 9 | 0.98 | $9.5 \times 10^{-4}$ | 0.10 | 1064 |
| 10 | 0.98 | $1.56 \times 10^{-3}$ | 0.16 | 1070 |
| 11 | 0.99 | $3.0 \times 10^{-3}$ | 0.31 | 1048 |
| 12 | 0.99 | $4.9 \times 10^{-3}$ | 0.50 | 1115 |
| 13 | 0.99 | $9.8 \times 10^{-3}$ | 1.00 | 1105 |
| 14 | 0.99 | $1.4 \times 10^{-2}$ | 1.41 | 1135 |
| 15 | 0.99 | $1.7 \times 10^{-2}$ | 1.72 | 1086 |
| 16 | 0.99 | $1.95 \times 10^{-2}$ | 1.97 | 1096 |
| 17 | 0.99 | $2.11 \times 10^{-2}$ | 2.13 | 1101 |

The column was subsequently washed with 1000 ml of completely desalted water, regenerated and washed neutral as described above. There were recovered in fractions 4–17 and in the regenerate or the wash waters together 99.4% of the charge of tartaric acid and maleic acid either as free acids or as their sodium salts.

A balance of the tests gives the following values:

| | |
|---|---|
| A. Charge dl-tartaric acid + maleic acid: | 13.49 mol |
| B. Charge maleic acid: | 0.28 mol; 2.076% of A |
| C. dl-tartaric acid + maleic acid product discharge 4–17: | 12.58 mol; 93.3% of A |
| D. Maleic acid in product discharge 4–17: | 0.0957 mol; 0.76% of C; 34.2% of B |

There were recovered 93.3% of the acids charged in discharging the anion exchanger. The difference to 99.4% is found in the wash waters and in the regenerate. The portion of maleic acid which was 2.076 mol % based on the total acids charged, was reduced to 0.76% in the discharge. This was 36.6% of the starting value. The capacity of the exchanger based on maleic acid under these conditions was 1.4 equivalents/1 resin.

The separating action of the anion exchanger can be even better utilized, if the loading is not carried out to the complete exhaustion of the exchanger. An exemplary balance for this case is therefore given based on the described test results in which only the charged solutions 1 and 2 were passed over the ion exhanger. There were obtained then fractions 4–13 and 278 grams of fraction 14 as the product.

| | |
|---|---|
| A. Charge dl-tartaric acid + maleic acid: | 9.623 mol |
| B. Charge maleic acid: | 0.1843 mol; 1.92% of A |
| C. dl-tartaric acid + maleic acid in the product: | 8.716 mol; 90.6% of A |
| D. Maleic acid in product: | 0.0249 mol; 0.286% of C; 13.5% of B |

Under these conditions 90.6% of the acids charged were found in the product; additionally 8.8% was recovered by washing and regenerating. Also the portion of maleic of 1.92%, based on the total acid content of the starting solution, was reduced to 0.286%; this was 14.9% of the starting value. The capacity of the ion exchanger under these conditions is then 1.18 equivalents maleic acid/1 resin.

The producer of the resin states that the total capacity of the resin used is 1.9 equivalents/1 and a usable capacity of 1.5 equivalents/1 resin.

EXAMPLE 7

The experiment was carried out analogously to example 6.

An aqueous solution 1 of the following composition was led via line 62 (FIG. 2) over the anion exchanger.

| Solution No. | Mol/l Dibasic Acids | Mol/l Maleic Acid | Mol % Maleic Acid | ppm Tungsten |
|---|---|---|---|---|
| 1 | 1.03 | 0.0187 | 1.82 | 710 |

Via line 64 (FIG. 2) after removing a diluted forerun 2 there was withdrawn fraction 3 in which the maleic acid concentration in relation to its portion in the acids in the starting solution is reduced about 84% whereby the tungsten is still completely separated off.

| Solution No. | Grams Amount | Mol/l Dibasic Acids | Mol/l Maleic Acid | Mol % Maleic Acid | ppm Tungsten |
|---|---|---|---|---|---|
| 2 | 779 | 0.21 | $<6 \times 10^{-5}$ | $<0.029$ | $<2$ |
| 3 | 6456 | 1.03 | 0.0031 | 0.30 | $<2$ |

In this example Mol/l of dibasic acids is based on the sum of dl-tartaric acid, maleic acid and tungstic acid. The mol % of maleic acid is as defined in example 6. The tungsten was added as tungstic acid for the production of solution 1.

After regenerating and washing as described in example 6 there was recovered in the product, i.e. in fractions 2 and 3 and in the regenerate 99.6% of the acids employed, in the regenerate they were recovered in the form of their sodium salts. The capacity of the ion exchange resin based on the maleic acid and tungstic acid separated off was 1.11 equivalents/l resin (compare example 6).

EXAMPLE 8

The experiment was carried out analogously to the procedure described in example 6.

An aqueous solution 1 of the following composition was led via line 62 (FIG. 2) over the anion exchanger.

| Solution No. | Mol/l Dibasic Acids | Mol/l Maleic Acid | Mol % Maleic Acid | ppm Tungsten |
|---|---|---|---|---|
| 1 | 1.05 | 0.0132 | 1.26 | 1790 |

Via line 64 after removing a diluted forerun 2 which resulted from the displacement of the water standing over the ion exchange resin, fractions were caught which had an increasing content of tungsten and maleic acid.

| Solution No. | Grams Amount | Mol/l Dibasic Acid | Mol/l Maleic Acid | Mol % Maleic Acid | ppm Tungsten |
|---|---|---|---|---|---|
| 2 | 429 | $<0.01$ | not detectable | not detectable | $<2$ |
| 3 | 406 | 0.76 | $<2 \times 10^{-5}$ | $<0.0026$ | $<2$ |
| 4 | 2033 | 1.04 | $9 \times 10^{-4}$ | 0.087 | $<2$ |
| 5 | 1082 | 1.04 | $1.94 \times 10^{-3}$ | 0.19 | $<2$ |
| 6 | 1076 | 1.04 | $3.82 \times 10^{3}$ | 0.37 | $<2$ |
| 7 | 1079 | 1.04 | $5.85 \times 10^{-3}$ | 0.56 | $<2$ |
| 8 | 1104 | 1.04 | $9.56 \times 10^{-3}$ | 0.92 | 3 |

The terms employed in the tables are defined in the same manner as in example 7.

After regeneration and washing in the manner described in example 6 there was recovered in the product, i.e., solutions 2-8, and in the regenerate 99.2% of the acids employed, in the regenerate they were recovered in the form of their sodium salts. There was obtained in the product 2-8 90.5% of the acids employed. On the average the maleic acid portion was 0.359%. At the same time it was reduced to 28.5% of its starting value, whereby the tungstic acid separation was still complete. The capacity of the resin based on the sum of the bound maleic acid and tungstic acid was the same as in example 7.

The process can comprise, consist essentially of or consist of the steps set forth using the stated materials.

What is claimed is:

1. A process for the production of pure racemic acid and mesotartaric acid comprising reacting an alkali maleate with aqueous hydrogen peroxide in a molar ratio of hydrogen peroxide to maleate of greater than 1:1 and also in the presence of an alkali tungstate as a catalyst to form the alkali metal salt of cis-epoxysuccinic acid in solution, passing the reaction solution thus formed over a strongly acidic cation exchanger to form free cis-epoxysuccinic acid and free tungstic acid, hydrolyzing the free cis-epoxysuccinic acid to form a hydrolysis mixture containing racemic acid and mesotartaric acid, removing the tungstic acid with an anion exchanger, crystallizing out the racemic acid from the tungstic acid free hydrolysis mixture by lowering the temperature of said hydrolysis mixture while retaining the mesotartaric acid in the mother liquor remaining after crystallization of the racemic acid and recovering the mesotartaric acid from the mother liquor.

2. The process of claim 1 including the step of regenerating the anion exchanger laden with tungstic acid with dilute aqueous alkali and returning the resulting solution of alkali tungstate to serve again as catalyst in forming the alkali metal salt of cis-epoxysuccinic acid.

3. The process of claim 2 including the step of treating the alkali tungstate solution formed in the regeneration of the anion exchanger with activated carbon to remove color-forming impurities therein.

4. The process of claim 1 comprising destroying excess hydrogen peroxide and other peroxygen compounds prior to forming the free cis-epoxysuccinic acid.

5. The process of claim 1 comprising carrying out the hydrolysis of the cis-epoxysuccinic acid in the presence of tungstic acid and removing the tungstic acid after the hydrolysis by passing the acid solution over an anion exchanger.

6. The process of claim 1 comprising removing the tungstic acid by passing the epoxysuccinic acid solution over an anion exchanger prior to the hydrolysis.

7. The process of claim 1 comprising aiding the crystallization of the racemic acid by evaporating a portion of the water.

8. The process of claim 1 comprising recovering the mesotartaric acid from the mother liquor by crystallization.

9. The process of claim 1 comprising recovering the mesotartaric acid from the mother liquor by evaporating said liquor to dryness.

10. The process of claim 1 wherein the molar ratio of hydrogen peroxide to maleic acid employed is between 1.01:1 and 5:1.

11. The process of claim 10 wherein the ratio of hydrogen peroxide to maleic acid is between 1.1:1 and 2:1.

12. The process of claim 11 wherein the ratio of hydrogen peroxide to maleic acid is between 1.1:1 and 1.3:1.

13. The process of claim 1 comprising destroying the excess hydrogen peroxide prior to forming the free cis-epoxysuccinic acid by passing the hydrogen peroxide and other peroxygen compounds containing reaction solution over a low porosity carrier catalyst consisting essentially of more than 90 weight % $SiO_2$ containing 0.01–5 weight % Pt at a temperature of 20°–100° C.

14. The process of claim 1 wherein the strongly acidic cation exchanger is a water insoluble sulfonated styrene polymer.

15. The process of claim 1 wherein the cation exchanger is a sulfonated styrene-divinyl benzene copolymer and is arranged in a plurality of beds said process comprising passing the reaction solution through at least two of said beds in succession.

16. The process of claim 1 comprising regenerating the cation exchanger with concentrated wash water from a previous cycle.

17. The process of claim 1 comprising recovering the racemic acid from the solution subsequent to the anion exchanger by fractional crystallization.

18. The process of claim 1 wherein the anion exchanger is a weakly basic ion exchange resin.

19. The process of claim 18 wherein the anion exchange resin is a water insoluble aminated styrene polymer.

20. The process of claim 19 wherein the anion exchange resin is an aminated styrene-divinyl benzene copolymer.

21. The process of claim 1 wherein there are employed two cation exchange columns in succession and two anion exchange columns in succession, said process comprising operating the first cation exchange column until break through of alkali while the second cation exchange column is maintained substantially fresh and then replacing said first cation exchange column, operating the first anion exchange column until break through of tungstic acid while the second anion exchange column is maintained substantially fresh and then replacing said first anion exchange column.

22. The process of claim 1 comprising saponifying the mother liquor after the crystallization of the racemic acid.

23. The process of claim 1 wherein the alkali maleate and alkali tungstate employed comprises an aqueous solution of alkali maleate and alkali tungstate obtained by passing an aqueous synthetic tartaric acid solution containing maleic acid and tungstic acid over a basic anion exchanger to separate the maleic acid and tungstic acid from the solution of tartaric acid, and thereafter removing the maleic acid and tungstic acid from the anion exchanger.

24. A process for separating maleic acid from an aqueous synthetic tartaric acid solution containing up to 5 mol % of said maleic acid comprising passing the impure tartaric acid solution over a basic anion exchanger in the hydroxyl or tartrate form.

25. The process according to claim 24 wherein the impure synthetic tartaric acid solution is free of catalyst employed to form the synthetic tartaric acid.

26. The process of claim 24 wherein the impure synthetic tartaric acid solution also contains catalyst for preparing the tartaric acid selected from the group consisting of molybdic acid and tungstic acid and said catalyst is also removed with the maleic acid from said impure tartaric acid solution.

27. The process of claim 26 wherein the catalyst is tungstic acid.

28. The process of claim 24 wherein the basic anion exchanger is a weakly basic ion exchange resin.

29. The process of claim 28 wherein the anion exchange resin is a water insoluble aminated styrene polymer.

30. The process of claim 29 wherein the anion exchange resin is an aminated styrene-divinyl benzene copolymer.

31. The process of claim 24 wherein the ion exchange is carried out at 20° to 50° C.

32. The process of claim 31 wherein the impure aqueous tartaric acid employed contains 10 to 20 weight % of tartaric acid.

33. The process of claim 24 wherein the impure aqueous tartaric acid contains maleic acid and a tartaric acid forming catalyst of the group consisting of molybdic acid and tungstic acid, the combined total of maleic acid and said catalyst being not over 5 mol %.

34. The process of claim 33 wherein the catalyst is tungstic acid.

35. The process of claim 1 comprising carrying out the reaction of alkali maleate with hydrogen peroxide in a circulatory reactor.

36. The process of claim 35 comprising carrying out the reaction of alkali maleate with hydrogen peroxide in two or more than two circulatory reactors in succession.

37. The process of claim 1 comprising carrying out the reaction of alkali maleate with hydrogen peroxide in two circulatory reactors in succession and in a subsequent flow tube.

* * * * *